(12) United States Patent
Melozzi

(10) Patent No.: US 9,700,418 B2
(45) Date of Patent: Jul. 11, 2017

(54) HIP PROSTHESIS

(71) Applicant: Alessandro Melozzi, Teramo (IT)

(72) Inventor: Alessandro Melozzi, Teramo (IT)

( * ) Notice: Subject to any disclaimer, the term of this patent is extended or adjusted under 35 U.S.C. 154(b) by 0 days.

(21) Appl. No.: 15/001,873

(22) Filed: Jan. 20, 2016

(65) Prior Publication Data

US 2016/0242914 A1    Aug. 25, 2016

(30) Foreign Application Priority Data

Feb. 4, 2015    (IT) .............................. AN2015A0008

(51) Int. Cl.
| | | |
|---|---|---|
| *A61F 2/32* | (2006.01) | |
| *A61F 2/36* | (2006.01) | |
| *A61F 2/34* | (2006.01) | |

(52) U.S. Cl.
CPC .............. *A61F 2/3609* (2013.01); *A61F 2/32* (2013.01); *A61F 2/34* (2013.01); *A61F 2/3601* (2013.01); *A61F 2002/3208* (2013.01); *A61F 2310/00023* (2013.01); *A61F 2310/00029* (2013.01)

(58) Field of Classification Search
CPC ...... A61F 2/32; A61F 2/34; A61F 2002/3225; A61F 2002/3208; A61F 2002/3216; A61F 2002/3414; A61F 2/36; A61F 2/30; A61F 2002/30242; A61F 2002/30378
USPC ............ 623/19.11–19.14, 21.13, 21.16, 23.4
See application file for complete search history.

(56) References Cited

U.S. PATENT DOCUMENTS

| | | | | |
|---|---|---|---|---|
| 3,916,451 A | * | 11/1975 | Buechel ................ | A61F 2/3854 403/56 |
| 3,992,726 A | * | 11/1976 | Freeman ............... | A61F 2/4225 623/23.4 |
| 4,135,517 A | * | 1/1979 | Reale ........................ | A61F 2/36 606/86 R |
| 4,179,758 A | * | 12/1979 | Gristina .................... | A61F 2/40 623/23.4 |
| 4,206,517 A | * | 6/1980 | Pappas ....................... | A61F 2/40 623/20.13 |
| 5,507,822 A | * | 4/1996 | Bouchon ............... | A61F 2/4241 606/62 |

(Continued)

FOREIGN PATENT DOCUMENTS

| | | |
|---|---|---|
| WO | 9107932 A1 | 6/1991 |
| WO | 2011006852 A1 | 1/2011 |

(Continued)

*Primary Examiner* — Alvin Stewart
(74) *Attorney, Agent, or Firm* — Egbert Law Offices, PLLC

(57) ABSTRACT

A hip prosthesis includes a stem intended to be inserted in the neck of the femur, a prosthetic head shaped as a substantially hemispherical cup, intended to be inserted in the acetabular seat, a distal prosthetic component connected to the stem and shaped as a substantially hemispherical cup with concavity towards the concavity of the prosthetic head, and a ball disposed between the distal prosthetic component and the prosthetic head in such manner to generate a ball coupling, wherein the prosthetic head includes a flattened pole that defines an external central flat planar surface in order to adjust to various shapes of the acetabular seat, grooves externally obtained to be coupled with the acetabular seat and holes to receive screws that are screwed into the acetabular seat.

15 Claims, 18 Drawing Sheets

(56) References Cited

U.S. PATENT DOCUMENTS

| | | | | |
|---|---|---|---|---|
| 5,593,445 A * | 1/1997 | Waits | A61F 2/3099 | 623/23.39 |
| 5,723,018 A * | 3/1998 | Cyprien | A61F 2/40 | 623/19.13 |
| 6,423,097 B2 * | 7/2002 | Rauscher | A61F 2/4241 | 623/21.15 |
| 6,454,808 B1 * | 9/2002 | Masada | A61F 2/4241 | 623/21.13 |
| 6,682,565 B1 * | 1/2004 | Krishnan | A61F 2/4241 | 623/21.16 |
| 7,033,396 B2 * | 4/2006 | Tornier | A61F 2/32 | 623/19.11 |
| 7,465,319 B2 * | 12/2008 | Tornier | A61F 2/32 | 623/19.11 |
| 7,914,580 B2 * | 3/2011 | Kellar | A61F 2/30767 | 623/16.11 |
| 8,142,511 B2 * | 3/2012 | Popoola | A61F 2/32 | 623/19.12 |
| 8,211,182 B2 * | 7/2012 | Linares | A61B 17/1617 | 623/22.15 |
| 8,277,511 B2 * | 10/2012 | Tornier | A61F 2/40 | 623/18.11 |
| 8,313,531 B2 * | 11/2012 | Termanini | A61F 2/34 | 623/22.15 |
| 8,377,142 B2 * | 2/2013 | Trail | A61F 2/4241 | 623/18.11 |
| 8,702,800 B2 * | 4/2014 | Linares | A61F 2/40 | 623/19.13 |
| 8,840,673 B2 * | 9/2014 | Linares | A61F 2/3804 | 623/20.11 |
| 8,840,676 B2 * | 9/2014 | Belew | A61F 2/4684 | 623/22.15 |
| 8,864,835 B2 * | 10/2014 | Linares | A61F 2/38 | 623/20.14 |
| 8,900,318 B2 * | 12/2014 | Linares | A61F 2/4225 | 623/21.15 |
| 9,114,018 B2 * | 8/2015 | Linares | A61F 2/42 | |
| 9,408,652 B2 * | 8/2016 | Hassler | A61B 17/1684 | |
| 9,427,321 B2 * | 8/2016 | Termanini | A61F 2/34 | |
| 2002/0143402 A1 * | 10/2002 | Steinberg | A61F 2/30742 | 623/22.16 |
| 2003/0158605 A1 * | 8/2003 | Tornier | A61F 2/4081 | 623/19.11 |
| 2004/0039449 A1 * | 2/2004 | Tornier | A61F 2/32 | 623/19.13 |
| 2004/0220673 A1 * | 11/2004 | Pria | A61F 2/4081 | 623/19.12 |
| 2005/0010303 A1 * | 1/2005 | Nogier | A61F 2/34 | 623/22.26 |
| 2005/0165490 A1 * | 7/2005 | Tornier | A61F 2/32 | 623/19.13 |
| 2005/0288791 A1 * | 12/2005 | Tornier | A61F 2/32 | 623/19.13 |
| 2008/0234830 A1 * | 9/2008 | Hershberger | A61F 2/3609 | 623/22.15 |
| 2009/0287309 A1 * | 11/2009 | Walch | A61B 17/15 | 623/18.11 |
| 2009/0292364 A1 * | 11/2009 | Linares | A61B 17/686 | 623/19.13 |
| 2010/0228355 A1 * | 9/2010 | Linares | A61B 17/1617 | 623/22.15 |
| 2012/0253467 A1 * | 10/2012 | Frankle | A61F 2/40 | 623/19.11 |
| 2012/0265319 A1 | 10/2012 | Prybyla et al. | | |
| 2012/0271425 A1 * | 10/2012 | Maurer | A61F 2/32 | 623/19.12 |
| 2012/0303130 A1 * | 11/2012 | Winslow | A61F 2/4081 | 623/19.12 |
| 2013/0053969 A1 * | 2/2013 | Linares | A61F 2/40 | 623/19.13 |
| 2013/0090736 A1 * | 4/2013 | Katrana | A61F 2/4014 | 623/19.13 |
| 2013/0090738 A1 * | 4/2013 | Linares | A61F 2/4261 | 623/21.13 |
| 2014/0128982 A1 * | 5/2014 | Termanini | A61F 2/34 | 623/19.13 |
| 2014/0236303 A1 * | 8/2014 | Maurer | A61F 2/32 | 623/19.12 |
| 2014/0257499 A1 * | 9/2014 | Winslow | A61F 2/4081 | 623/19.13 |
| 2015/0335440 A1 * | 11/2015 | Linares | A61F 2/40 | 623/19.12 |
| 2016/0374815 A1 * | 12/2016 | Siccardi | A61F 2/40 | 623/19.12 |

FOREIGN PATENT DOCUMENTS

| | | |
|---|---|---|
| WO | 0170141 A1 | 9/2011 |
| WO | 2011112353 A1 | 9/2011 |

* cited by examiner

HIP PROSTHESIS

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present patent application for industrial invention relates to a hip prosthesis conceived in such a way to save as much as possible the bone stock of the femur proximal end and without giving the complications that are found in other prosthetic types, such as coating prostheses.

2. Description of Related Art Including Information Disclosed Under 37 CFR 1.97 and 37 CFR 1.98.

As it is known, the anatomy of the proximal femur has a spheroid surface called "femoral head", which articulates with a cavity of dimensions corresponding to the femoral head, situated in the pelvis, called cotyle or acetabulum. These two anatomic formations make up the coxofemoral joint.

When it cannot be treated with medications or physiotherapy, the deterioration of the joint because of fractures or degenerative processes (coxarthrosis) finds a solution in the implant of a prosthesis.

A typical hip prosthesis is made up of three components:
- a femoral component composed of a stem that is pressed inside the femoral channel which is suitably modeled with progressive milling to generate a seat having the same shape as the stem; alternatively, a similarstem is cemented;
- a prosthetic head that is fixed onto the stem with a locking system technically known as "Morse taper";
- an acetabular cup complete with insert that articulates with the corresponding prosthetic head.

The stem of the hip prosthesis is generally made of metal (normally titanium alloy), has a length of approximately 12-15 cm and a shape similar to the anatomic cast of the femoral channel. After being pressed inside the femoral channel, the stem is firmly fitted, adhering on the internal walls of the bone corticals. In order to introduce a stem of this type it is necessary to resect the femoral neck at the base and mill the inside of the femoral channel removing a large quantity of bone by using progressive rasps specific for each type of prosthesis.

US2004/0039449 discloses a prosthesis that does not save the neck of the femur. In fact the neck is totally removed. A long channel is obtained in the femur, wherein a long prosthetic stem is inserted. Such a prosthesis is not suitable for being mounted in the femur neck because it is implanted in the femoral channel.

In order to solve these drawbacks, in recent years the so-called "neck saving" prostheses have been implanted, wherein the size and shape of the stem are conceived in such a way that resection is performed not at the base of the femoral neck, but at the base of the femoral head, implanting a stem that is able to anchor in the metaphisiary region without attacking the femoral channel.

WO91/07932 discloses a prosthesis that saves the neck of the femur. A spherical head is fixed to the stem, resting on the corticals of the femoral neck, with the risk of reabsorption. On the spherical head an acetabular segment with hemispherical shape can slide. However, this type of configuration is impaired by regulation problems. The femoral stem ends with a "Morse taper" whereon the prosthetic head made of metal or ceramic is inserted, being articulated with the acetabular component. The acetabular component is formed of a metal cup that is fixed to the pelvis, either by means of pressure or screwing, after suitably boring the natural cotyle. In the metal cup a ceramic or polyethylene insert is positioned, which articulates with the prosthetic head.

WO2011/006852, in the name of the applicant, discloses a hip prosthesis suitable for saving the femoral neck. However, the acetabular cup cannot be implanted on all patients, especially in patients with dysplastic or low-depth acetabula. In fact, the prosthetic head is shaped as a hemispherical cap with a perfectly smooth external surface. Said prosthetic head has a double sphericity, i.e. a central portion is provided on the external surface of the prosthetic head, in correspondence of the hemisphere pole, which protrudes outwards, having a surface with substantially ovoidal or ellipsoidal profile to reproduce as much as possible the anatomy of the femoral head in order to adjust in the acetabular seat.

WO2011/112353 discloses a hip prosthesis that is similar to the one described in WO2011/006852. Such a hip prosthesis comprises a prosthetic head or acetabular cup that is perfectly hemispherical and smooth and provided with holes for screws used for fixing to the acetabular seat. The acetabular cup comprises a very long shank that is fixed to a ball, in such manner to define a gap between ball and acetabular cup, wherein a femoral cup can slide. In such a case, the stress suffered by the acetabular cup is completely discharged on the shank that is fixed to the ball. For this reason the shank must be very long (a length higher than the radius of the ball) and the ball must be very small with a diameter lower than 40 mm, i.e. a diameter lower than the diameter of a natural head of a femur.

Hip prostheses are known having an acetabular component that comprises a non-cemented metal cup coated with a porous material that stimulates the re-growth of the bone and a stem that receives a femoral head for the hip joint. The surgical technique used to implant the acetabular component provides for the following steps:
- boring the natural cotyle with sharp mills in order to obtain an acetabular seat,
- using a test prosthesis to identify the correct size of the acetabular component,
- implanting the final prosthesis either by means of pressure or screwing in the acetabular seat obtained in the pelvis.

In the implanted metal cup a ceramic or polyethylene insert is positioned, which articulates with the prosthetic head implanted on the femoral stem. The drawbacks of such a traditional prosthesis are the early detachment of the prosthesis caused by wear or failure of the insert of the acetabular cup and a high percentage of dislocations caused by the incorrect position of the prosthesis. The dislocation of a hip prosthesis occurs when the prosthetic head comes out of the acetabular seat called "cotyle". The causes of a dislocation of the total hip prosthesis are several:

- the prosthesis is not positioned correctly and is often instable,
- extreme bending and rotation movements must be avoided especially immediately after the operation,
- the access ways are more or less dislocating.

US2012/265319 discloses an acetabular prosthesis with a flattened pole and an external roughened surface.

WO01/70141 discloses an acetabular cup with a flattened pole and ribs extending on the external surface to stabilize the prosthesis.

The object of the present invention is to eliminate the drawbacks of the prior art by disclosing a hip prosthesis that is able to save the neck of the femur and is versatile and suitable for being applied to various types of acetabular seats.

Another object of the present invention is to provide such a hip prosthesis that is reliable, long-lasting and capable of not dislocating the femur when the prosthesis is positioned.

BRIEF SUMMARY OF THE INVENTION

These purposes are achieved according to the invention with the characteristics claimed in independent claim 1.

Advantageous embodiments appear from the dependent claims.

The hip prosthesis according to the invention comprises:
- a stem intended to be inserted in the neck of the femur,
- a prosthetic head shaped as a substantially hemispherical cup, intended to be inserted in the acetabulum,
- a distal prosthetic component connected to the stem and shaped as a substantially hemispherical cup with concavity towards the concavity of said prosthetic head, and
- a ball disposed between said distal prosthetic component and said prosthetic head, in such manner to generate a spherical coupling.

The prosthetic head comprises:
- a flattened pole defining an external central flat and planar surface in order to adapt to various shapes of acetabular seat,
- a central portion with higher thickness than a peripheral portion of the prosthetic head, in such manner to generate a step inside the prosthetic head.

The central portion of the prosthetic head is engaged on the external surface of the ball in such manner to generate an empty space between the external surface of the ball and the internal surface of the peripheral portion of the prosthetic head, so that the border of said distal component is introduced in said empty space.

The prosthetic head also comprises:
- grooves to anchor the prosthetic head to the acetabular seat in order to obtain a primary stability of the prosthetic head, and
- through holes to receive fixing screws used to fix the prosthetic head to the acetabular seat.

The through holes are exclusively obtained in said central portion of the prosthetic head and said grooves are exclusively obtained in said peripheral portion of the prosthetic head.

In this way the higher thickness of the central portion with respect to the peripheral portion of the prosthetic head is used for two purposes:
- to obtain a spacing element with respect to the ball in such manner to generate the empty space wherein the distal cup slides,
- to obtain more resistant and more reliable seats for the fixing screws.

Moreover, by engaging on the ball, the central portion of the prosthetic head ensures an equal load distribution between the prosthetic head and the ball, thus allowing for making balls with large dimensions, including with diameter higher than 40 mm, i.e. balls with dimensions substantially similar to the natural head of a femur.

Advantageously, the prosthetic head has a roughened external surface that is coupled with the acetabular seat to allow the regenerated bone of the acetabular seat to grow inside the roughened surface in order to give a secondary stability to the prosthesis.

The advantages of the present invention are evident, wherein the prosthetic head has been given a hemispherical shape with a flattened pole. The prosthetic head has a roughened external surface for a good osteointegration of the bone.

Moreover, the prosthetic head is provided with through holes for fixing screws (therefore with the possibility to implant and adapt the prosthesis to all patients, including dysplasic ones).

The prosthesis of the invention is not impaired by the drawbacks of the prostheses of the prior art for the following reasons:
- null consumption of the sliding parts thanks to the spherical coupling between the distal prosthetic component and the ball, and
- elimination of all dislocation risks thanks to the provision of the ball with a diameter of natural size similar to the diameter of a femoral head; in fact, when a head with large diameter is implanted, the possibilities for the prosthesis to dislocate are much lower compared to a prosthesis with a head having a small diameter.

BRIEF DESCRIPTION OF THE SEVERAL VIEWS OF THE DRAWINGS

Additional characteristics of the invention will appear from the detailed description below, which refers to merely illustrative, not limiting, embodiments, illustrated in the attached drawings, wherein.

DETAILED DESCRIPTION OF THE INVENTION

Figure 1:
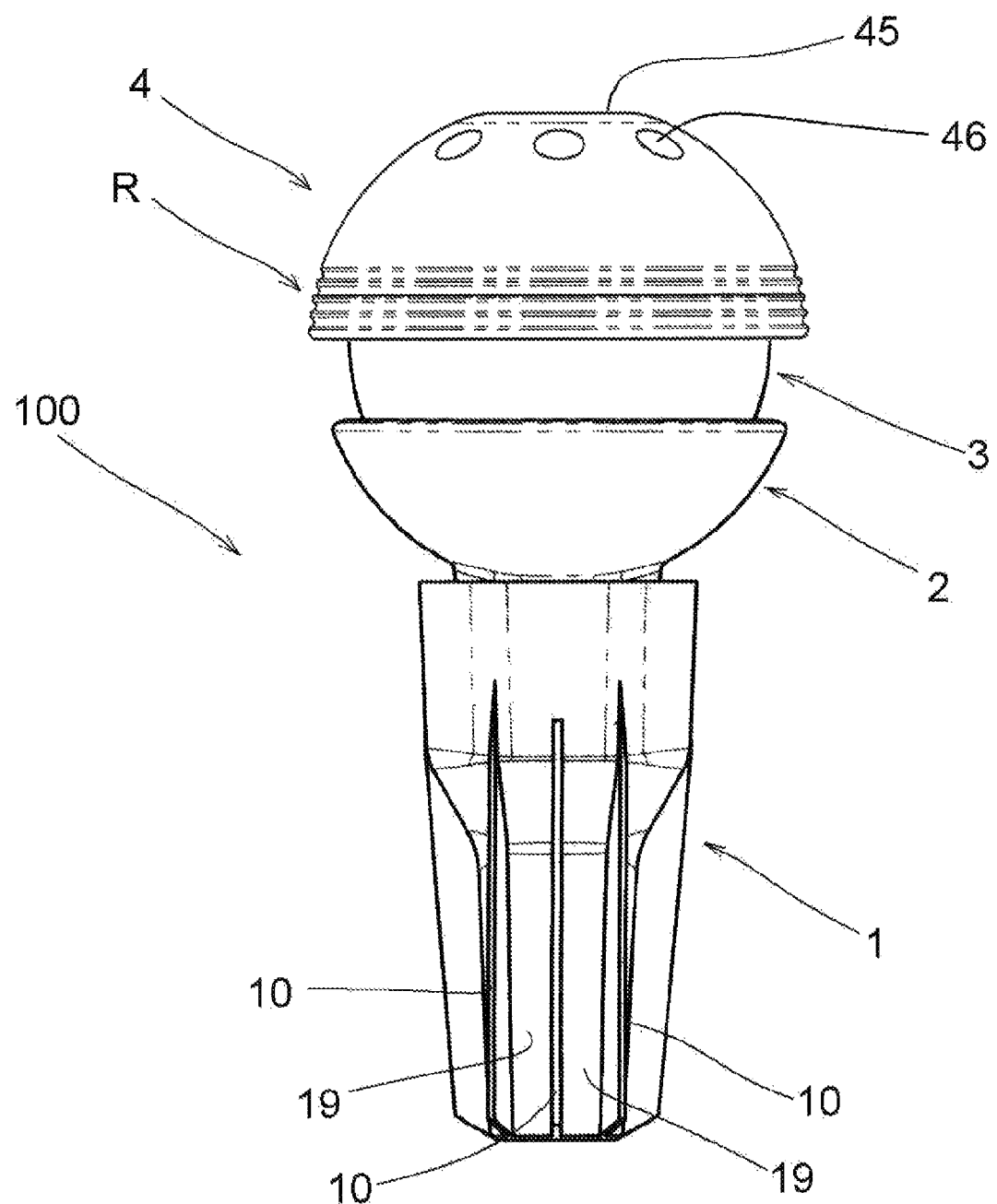
FIG. 1 is a front view of a prosthesis according to a first embodiment of the invention.

With reference to FIGS. 1 to 6 a first embodiment of a prosthesis according to the invention is disclosed, generally indicated with reference numeral (100).

The prosthesis (100) comprises:
- a stem (1) intended to be fixed in the neck (60) of a femur (6),
- a distal prosthetic component (2) shaped as a substantially hemispherical cup and intended to be coupled with the stem (1),
- a ball (3) intended to be disposed inside said distal prosthetic component (2) in such manner to generate a spherical coupling, and
- a prosthetic head (4) with hemispherical shape and intended to be coupled with said ball (3).

Referring to FIG. 1, the stem (1) has a truncated-conical shape and is provided with longitudinal wings (10) that radially protrude outwards to penetrate the spongy tissue of the femur neck. Empty spaces (19) are defined between the wings (10) and are used for anchoring in the spongy tissue.

Figure 2:
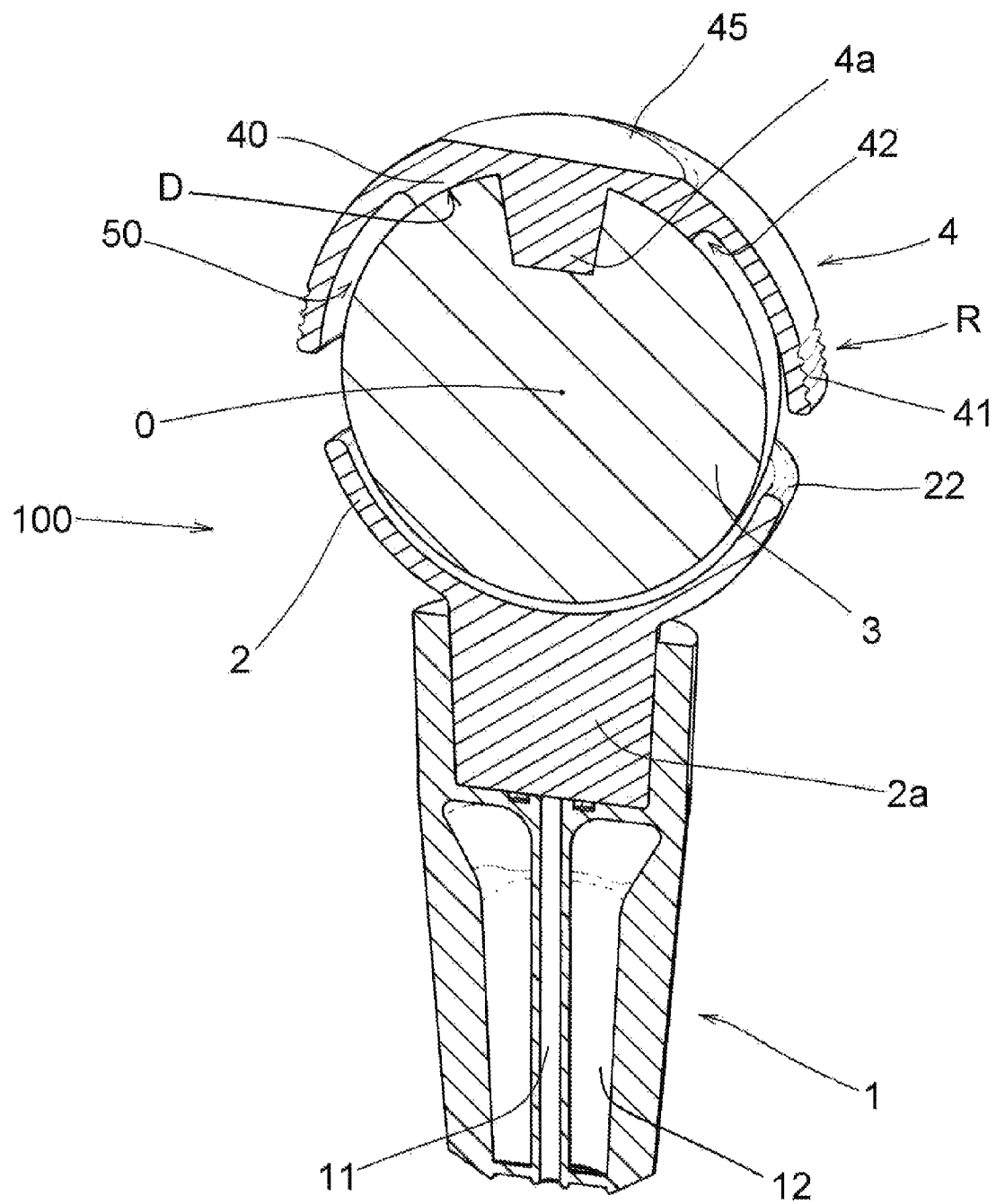
FIG. 2 is an axial sectional view of the prosthesis of FIG. 1.

Referring to FIG. 2, an axial channel (11) is obtained inside the stem in order to introduce a guiding thread. The stem (1) has seats (12) that are open on the bottom to allow for the access of spongy tissue.

Figure 3:
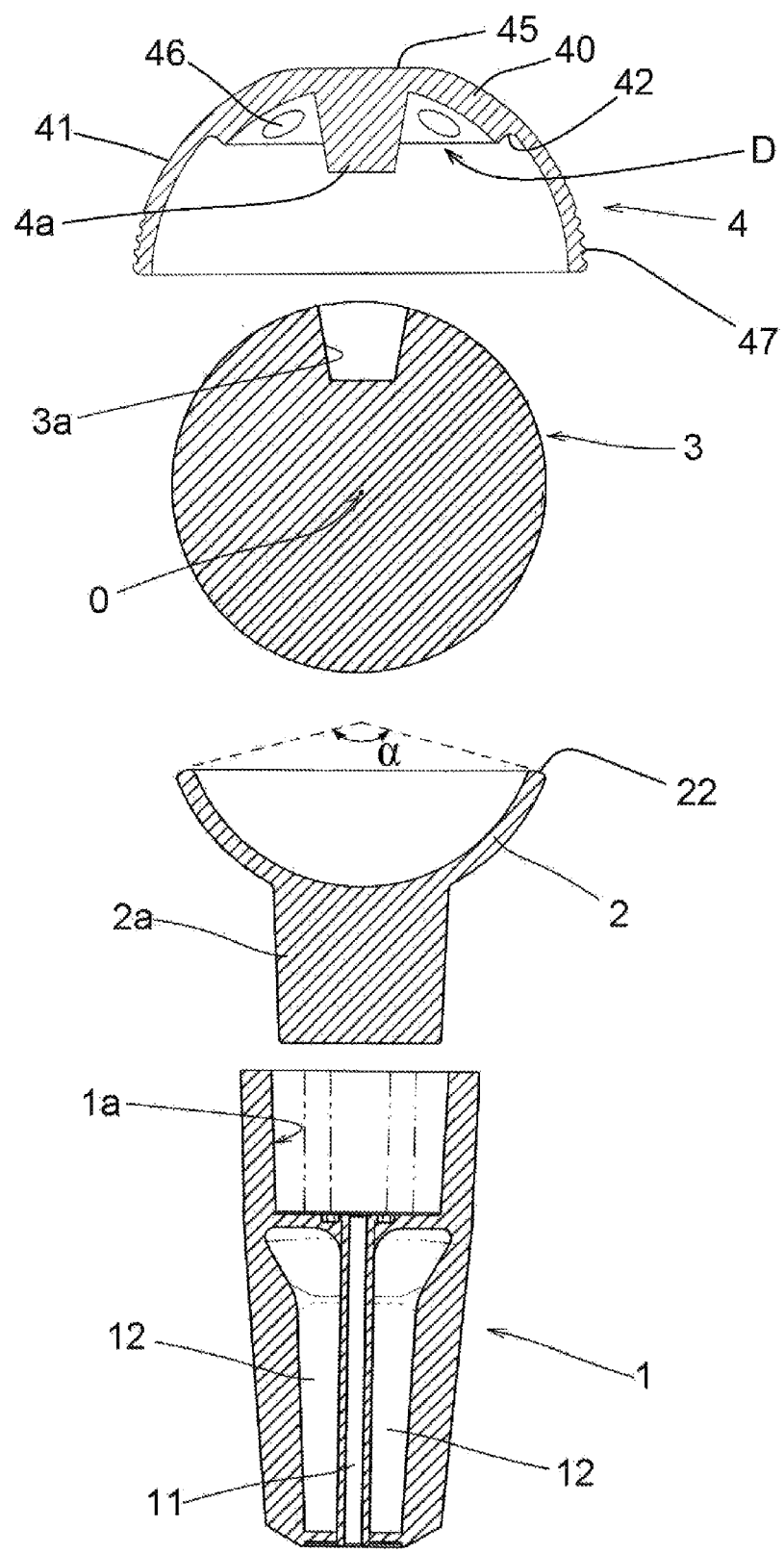
FIG. 3 is an exploded axial sectional view of the prosthesis of FIG. 2.

Referring to FIG. 3, a truncated-conical seat (la) is obtained at the upper end of the stem, wherein a truncated-conical shank (2a) is inserted by means of pressure, protruding in lower position from the distal prosthetic component (2), hereinafter defined as distal cup (2). Although it is not shown in the figures, the shank (2a) of the distal cup can be internally empty, with a cavity shaped as a traditional Morse taper to allow for coupling with the stem (1) shown in the drawings and also with traditional stems provided with an end shaped as a Morse taper.

As shown in FIG. 3, in a sectional view, the distal cup (2) is shaped as an arc of circle with a central angle (a) slightly lower than 180°. Preferably, the central angle (a) is higher than 160° to maximize the sliding surface of the ball (3) and therefore minimize friction between the distal cup (2) and the ball (3).

The ball (3) has a perfectly spherical external surface, i.e. a circular section with center (O). The ball (3) has a truncated-conical hole (3a) wherein a truncated-conical shank (4a) is fixed by means of pressure, radially protruding inwards from the central part of the prosthetic head (4).

The prosthetic head (4) is shaped as a hemispherical cap with a flattened pole (45). In a sectional view, the prosthetic head (4) is an arc of circle subtended by a central angle of approximately 180° with the flattened pole (45). An external circular portion (45) with a flat planar surface in order to adjust to all types of acetabular seat is provided in the external surface of the prosthetic head (4). The flattened pole (45) is substantially disposed at a latitude of 70-80°.

The prosthesis (100) comprises spacing means (5 D) disposed between the ball (3) and the prosthetic head (4) in such manner to generate an empty space (50) between the external surface of the ball (3) and the internal surface of the prosthetic head. In fact, the distal cup (2) must be able to slide in the empty space (50).

The spacing means (D) are obtained in one piece with the prosthetic head (4) by means of a central portion (40) of the prosthetic head (4) around the shank (4a). Such central portion (40) of the prosthetic head has a higher thickness than a peripheral portion (41) in such manner to generate a step surface (42). Therefore the empty space (50) is formed between the ball (3) and the peripheral portion (41) of the prosthetic head.

Advantageously, the central portion (40) has a thickness double than the peripheral portion (41). For example, the central portion (40) has a thickness of 4 mm, whereas the peripheral portion (41) has a thickness of 2 mm. Moreover, the thickness of the proximal cup (2) is slightly lower than the thickness of the peripheral portion (41) of the prosthetic head or in any case slightly lower than the thickness of the step (42) of the prosthetic head.

Referring to FIG. 2, when the prosthetic head (4) is mounted on the ball (3), the central portion (40) of the prosthetic head stops against the external surface of the ball (3), consequently generating the empty space (50) between the external surface of the ball (3) and the internal surface of the peripheral portion (41) of the prosthetic head. Said empty space (50) is intended to receive the border (22) of the distal cup (2) that slides on the ball (3). When part of the distal cup (2) is situated in the empty space (50), it is perfectly guided by the ball (3) and by the prosthetic head (4).

Normally the distal cup (2) is totally outside of the prosthetic head (4). In any case, when the border (22) of the distal cup is inside the empty space (50), most of the distal cup (2) is always outside of the prosthetic head (4).

Referring to FIG. 2, in normal conditions, the axis of the shank (4a) of the prosthetic head coincides with the axis of the shank (2a) of the distal cup and the axis of the channel (11) of the stem.

It must be noted that the center of the radius of curvature of the distal cup (2), the center (O) of the ball (3) and the center of the radius 5 of curvature of the prosthetic head (4) coincide. Such a configuration provides high freedom of rotation without impingement, a perfect adjustment of the prosthesis, a simple installation and at the same time it maximizes the sliding surfaces.

Figure 4:
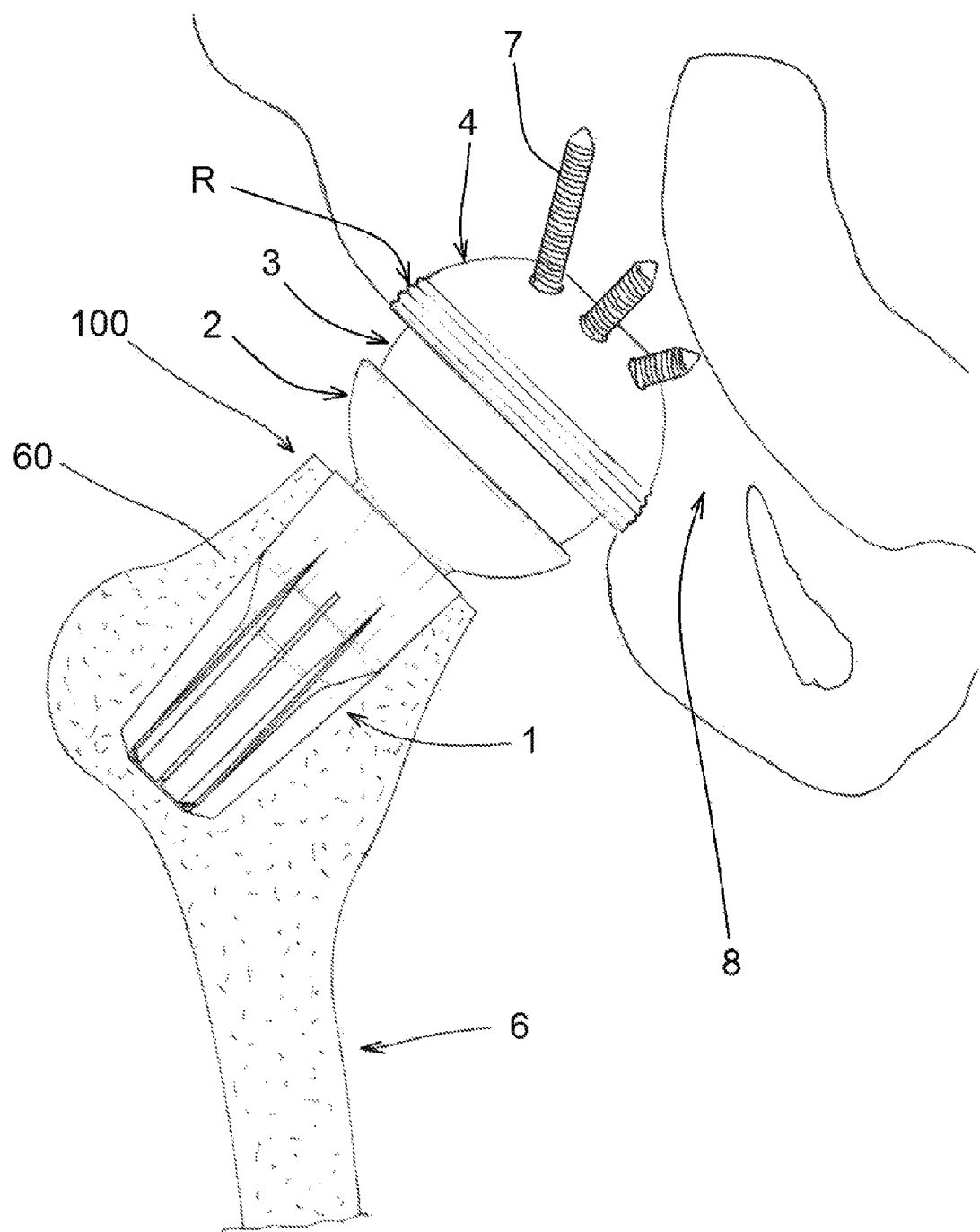
FIG. 4 is a diagrammatic view of the prosthesis of FIG. 1 inserted in the neck of a femur.

FIG. 4 shows the prosthesis (100) mounted in the neck (60) of the femur (6). As shown in the figure, such a type of prosthesis allows for saving the neck (60) of the femur. The stem (1) must have a length lower than 65 mm and has been especially designed to anchor to the spongy tissue of the femoral neck. FIG. 4 also shows an acetabular seat or cotyle (8) wherein the prosthetic head (4) is fixed, generally with press-fit.

Figure 5:
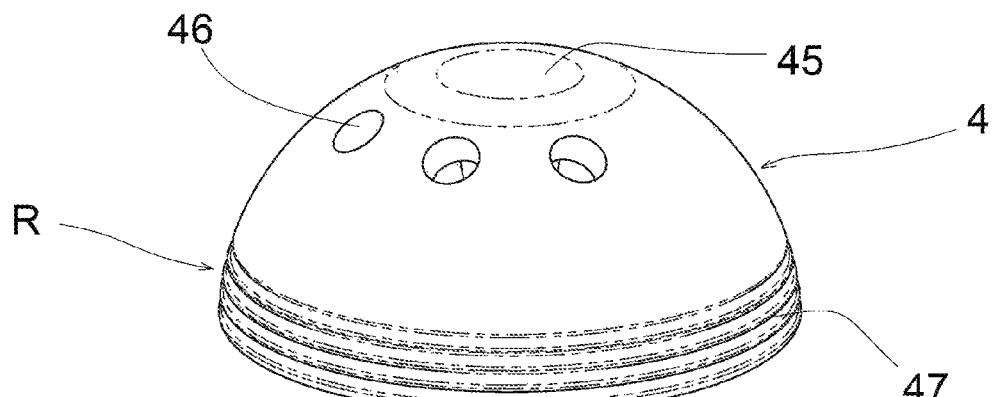
FIG. 5 is a perspective view of an acetabular cup of the prosthesis of FIG. 1.
Figure 6:
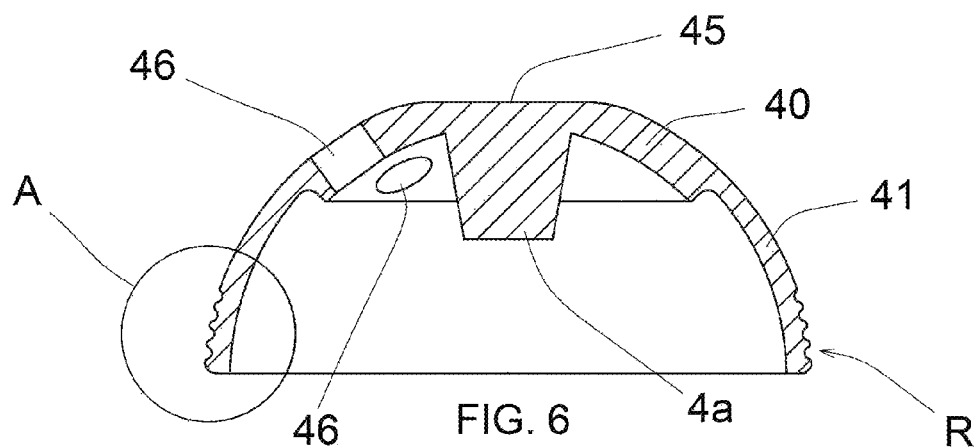
FIG. 6 is an axial sectional view of the acetabular cup of FIG. 5.

With reference to FIGS. 5 and 6, the prosthetic head (4) comprises holes (46) obtained in the central portion (40) of the prosthetic head, but externally with respect to the flattened pole (45) of the prosthetic head. For illustration purposes, the holes (46) are angularly spaced by 45° and are in number of three. The holes (46) are used to receive fixing screws (7) (FIG. 4) that are fixed in the cotyle (8). The fixing screws (7) ensure a primary stability to the acetabular seat (8), when the press-fit of the prosthetic head (4) in the acetabular seat (8) does not give an acceptable stability. The screws (7) are implanted in the cotyle (8) by means of suitable drills that generate holes in the acetabular seat (8). The screws (7) are screwed between the bottom of the prosthetic head (4) and the portion of good bone of the pelvis in such manner to make the implant stable.

Figure 6A:
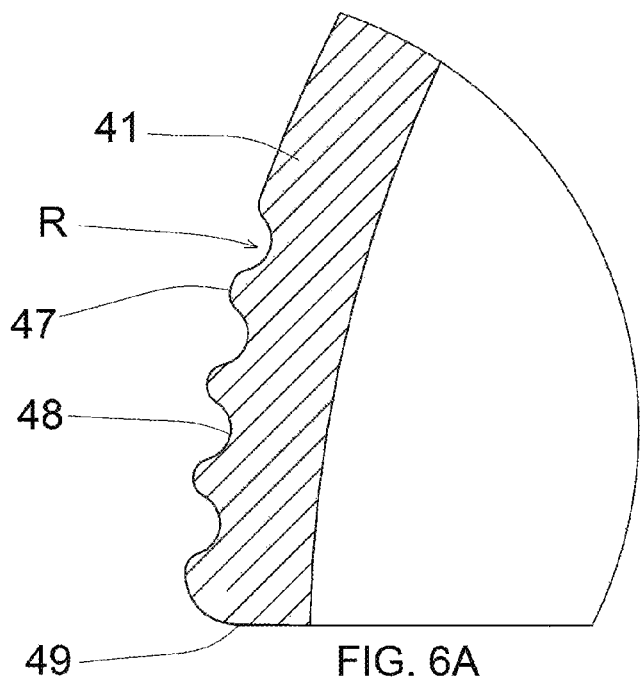
FIG. 6A is an enlarged detail enclosed in the circle (A) of FIG. 6.

Referring to FIG. 6A, the prosthetic head (4) also comprises grooves (R) obtained in the external surface of the prosthetic head. The grooves (R) ensure the primary anchoring of the prosthetic head (4) to the acetabular seat (8). To that end the acetabular seat (8) is prepared with suitable drills that are one size smaller than the prosthetic head. Therefore, a primary stability of the prosthesis is created with a press-fit coupling between the prosthetic head and the acetabular seat during the installation. Such a primary stability is improved with the fixing screws (7) that are engaged in the holes (43) of the prosthetic head and are tightened in the acetabular seat (8).

The grooves (R) are disposed in a lower portion of the 5 prosthetic head, i.e. in an equatorial zone of the prosthetic head which has the higher diameter, i.e. in the peripheral part (41) with lower thickness of the prosthetic head. The grooves (R) are circumferential grooves (48) obtained with notches on the external surface from the prosthetic head, starting from the lower border (49) of the prosthetic head. In such a way each circumferential groove (48) is defined between the two circumferential ribs (47). In a cross sectional view, the circumferential ribs (47) and the circumferential grooves (48) have a substantially arched or sinusoidal or saw tooth shape.

The grooves (R) are obtained in the peripheral part (41) of the prosthetic head and extend from the lower border (49) of the prosthetic head until a latitude of about 20°-30°. For illustrative purpose four circumferential ribs (47) and four circumferential grooves (48) are provided.

Figure 19:
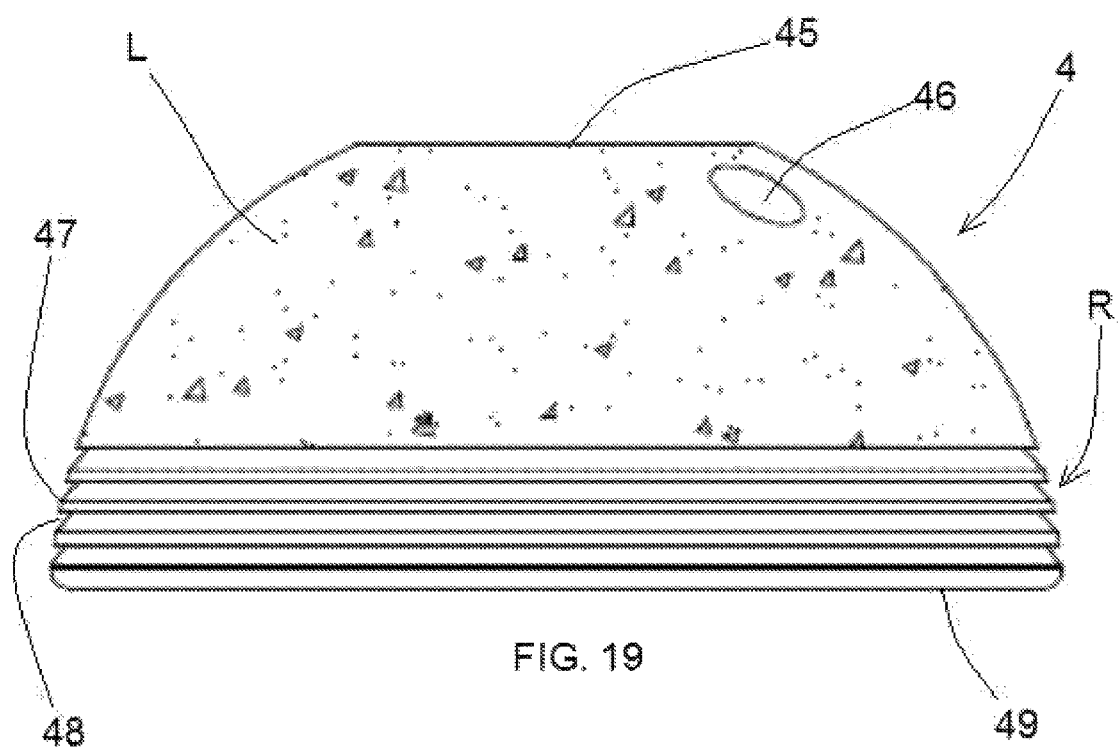
FIG. 19 is a front view of an embodiment of the prosthetic head.

Referring to FIG. 19, the grooves (R) are circumferential circular concentric grooves (48) and define circumferential ribs (48) with a tapered shape, with increasing dimensions towards the lower border (49) of the prosthetic head. In a sectional view, the circumferential ribs (47) have a triangular saw tooth shape. In this way the press-fit coupling between the prosthetic head (4) and the acetabular seat (8) is facilitated, preventing the prosthetic head from being pulled-out, detached or dislocated from the acetabular seat.

Figure 20:
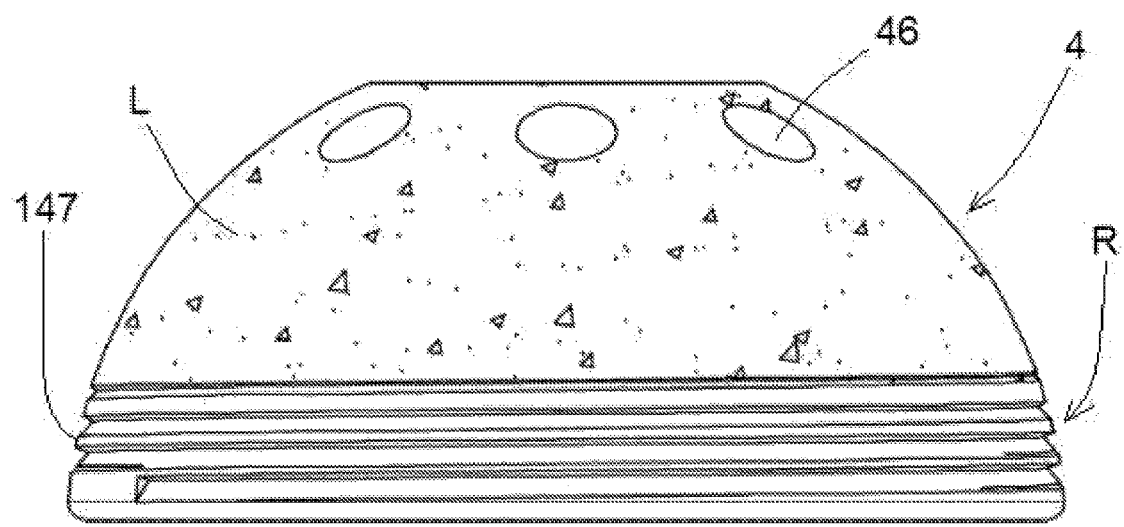
FIG. 20 is the same view as FIG. 19, showing another embodiment of the prosthetic head.

As shown in FIG. 20, the grooves (R) are grooves defined by a helical thread (147) that is wound around the external surface of the prosthetic head. The thread (147) is of self-tapping type. In this way the prosthetic head (4) is screwed into the acetabular seat (8), preventing the prosthetic head from being pulled-out, detached or dislocated from the acetabular seat.

As shown in FIGS. 19 and 20, the prosthetic head (4) has a roughened surface (L) that extends on the entire external surface of the prosthetic head, except for the grooves (R). The roughened surface (L) allows the regenerated bone to grow and ensures a secondary stability of the prosthesis (100) as the regenerated bone grows on the roughened surface (L) of the prosthetic head.

The roughened surface (L) can be made with the same material as the prosthetic head (4) or with a coating material of the prosthetic head. For illustration purposes the prosthetic head (4) is made of chrome-cobalt alloy, titanium alloy or Trabecular Titanium.

If the prosthetic head is made of trabecular titanium, the roughened surface (L) is obtained with a coating of hydroxyapatite on trabecular titanium.

Instead, if the prosthetic head is made of chrome-cobalt alloy or titanium alloy, the roughened surface (L) is obtained with a coating of porous titanium powder and with a coating of hydroxyapatite on the prosthetic head of chrome-cobalt alloy or titanium alloy. Hydroxyapatite is a rare mineral with chemical composition $Ca_5(PO_4)_3(OH)$. Hydroxyapatite can be used as filler to replace amputated bones or as coating to stimulate the bone growth in prosthetic implants.

The surgical technique is described hereinafter.

After making a pre-operation planning, with suitable transparencies, the measurements of the stem (1) and of the prosthetic head (4) are chosen. The measurements of the ball (3) and of the distal cup (2) are calculated based on the measurements of the prosthetic head (4).

After making a dislocation maneuver of the femoral epiphysis, the resection level of the osteotomy is determined. The length of the osteotomy is determined according to the system chosen in the pre-operation planning. The osteotomy of the femoral head is made precisely at the base of the head, in such manner to have a full visibility of the femoral neck in its projections.

Anatomical landmarks are traced on the osteotomy plane with a suitable instrument in such manner to perfectly identify the center of the femoral neck. A guiding thread is introduced in the femoral neck and passed beyond the neck and the opposite cortical is perforated under the greater trochanter in such manner to obtain a stability while passing the rasps.

The spongy tissue contained in the femoral neck is perforated with a small drill, creating an invitation for the rasps that will prepare the seat for the final prosthesis.

After preparing the final seat of the prosthesis with the rasps inside the neck of the femur (60), the stem (1) of the prosthesis is chosen, according to the measurement of the last rasp used and the prosthesis is directly taken out of a sterile package. Using a suitable impactor/extractor that uses the male Taper cone (2a) of the distal cup, introduced in the seat (la) of the stem, a threaded handle of the stem is rotated, blocking it in an internal recess of the prosthesis. The final implant is made.

The acetabulum or cotyle (8) is prepared after implanting the stem. The bottom of the cotyle is milled with suitable increasing circular drills, creating a seat for the prosthetic head (4).

After the last drilling, the acetabular bottom is measured with test heads in order to select the prosthetic head (4).

After determining the measure of the prosthetic head (4), the ball (3) and the prosthetic head (4) assembly is taken from its sterile package. Using a suitable impactor/extractor that uses the male Taper cone (4a) of the prosthetic head, being screwed onto it, the final implant is made.

After implanting the prosthetic head (4), reduction and stability tests are made with a test ball and distal cup. After establishing the final length of the ball (3), the prosthesis is taken from its sterile package for the final implant. After implanting the ball (3), the distal cup (2) corresponding to the ball (3) to be connected to the stem (1) with Morse taper (2a) is chosen. The screws (7) are used in case of a slight instability caused by the poor quality of the bone during the implant of the prosthetic head (4). The inside of the holes (46) of the prosthetic head are milled with suitable tools, after checking the correct size of the screw (7) with a suitable instrument (depth measuring device), the sterile package of the screw is opened and the screw is implanted with a cardan screwdriver. After tightening the screws (7) and stabilizing the prosthetic head (4), the ball (3) and the distal cup (2) are implanted, the prosthesis is reduced, and the length of the limb and the stability of the prosthesis are checked in order to avoid the dislocation of the prosthesis.

Hereinafter elements that are identical or correspond to the elements described above are indicated with the same reference numbers, omitting their detailed description.

Figure 7:
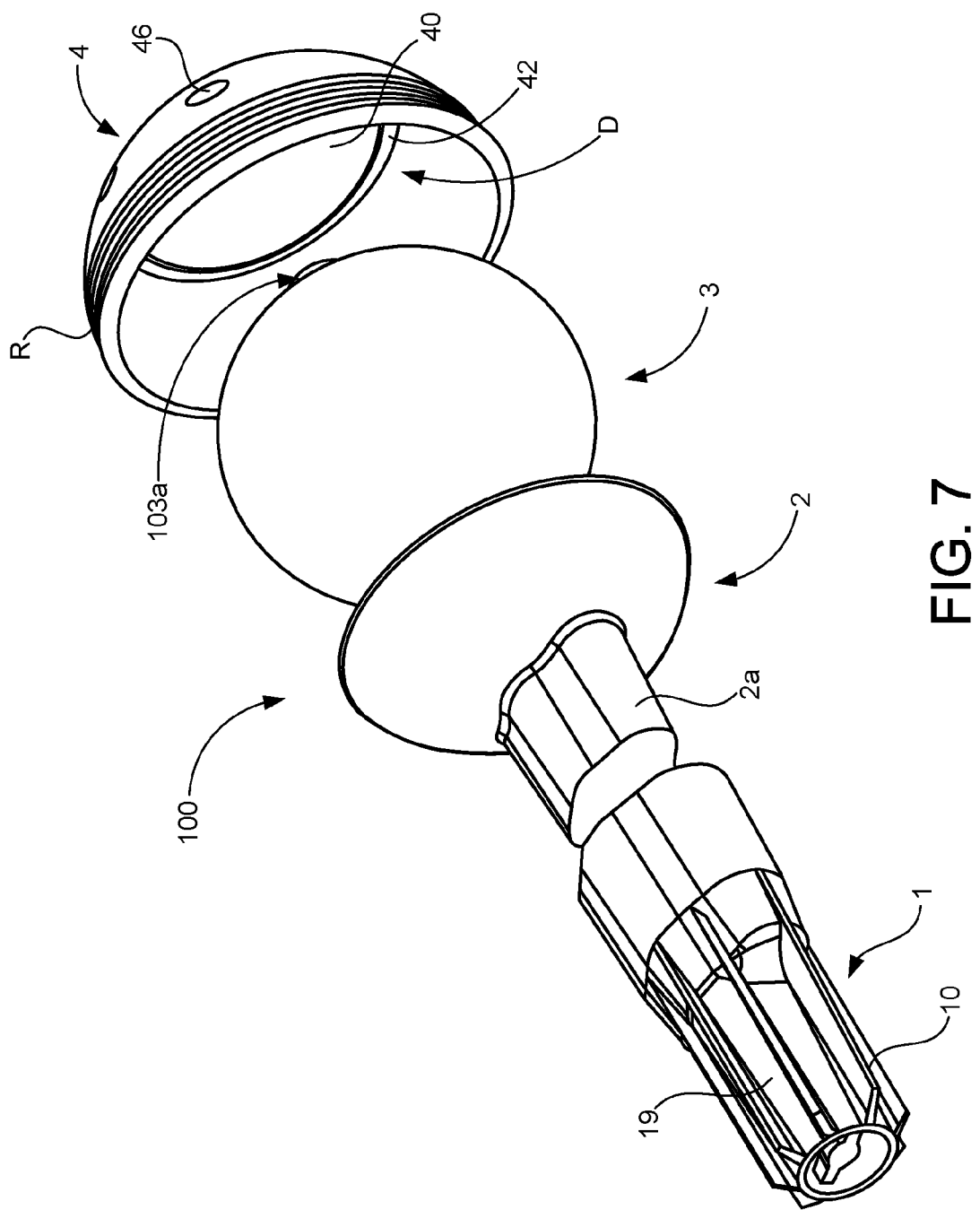
FIG. 7 is an exploded perspective view of a version of the prosthesis of FIG. 1.
Figure 8:
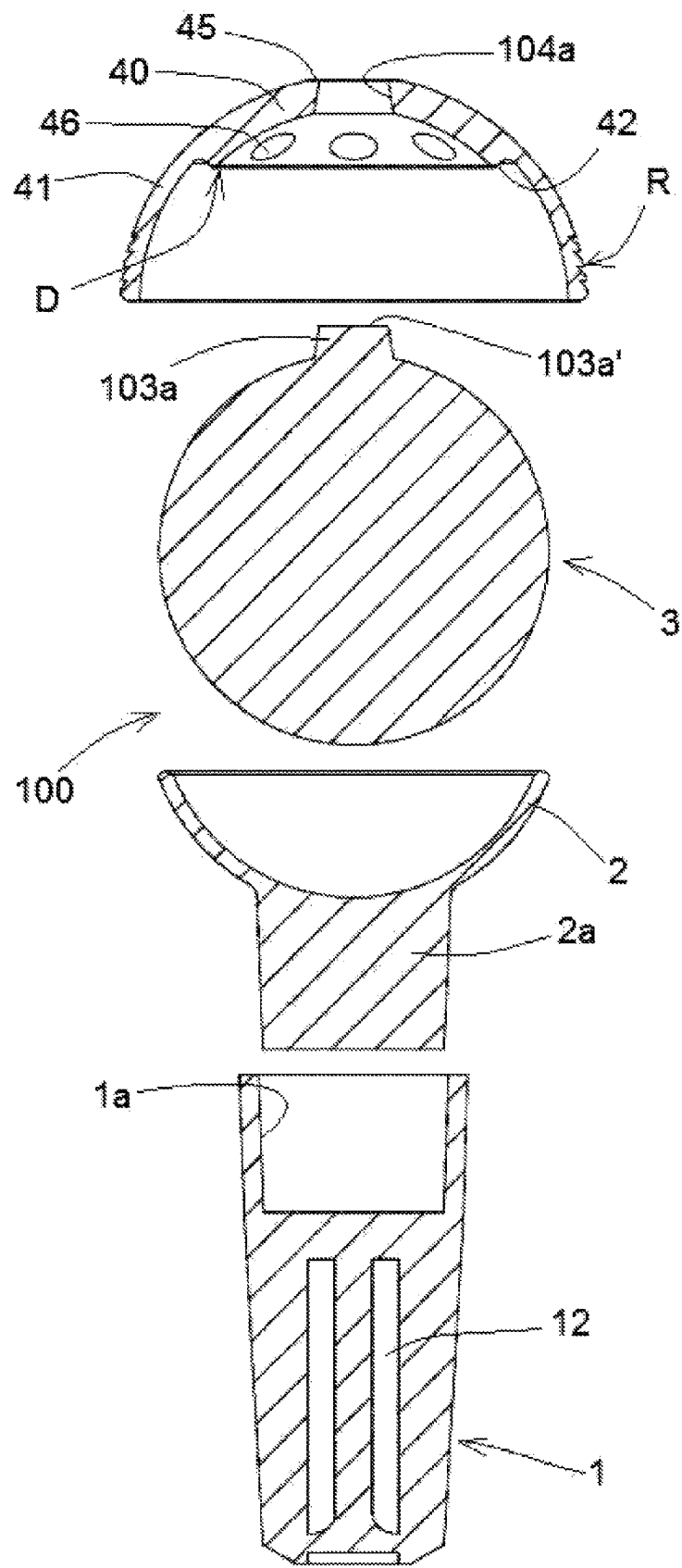
FIG. 8 is an axial sectional view of the prosthesis of FIG. 7.
Figure 9:
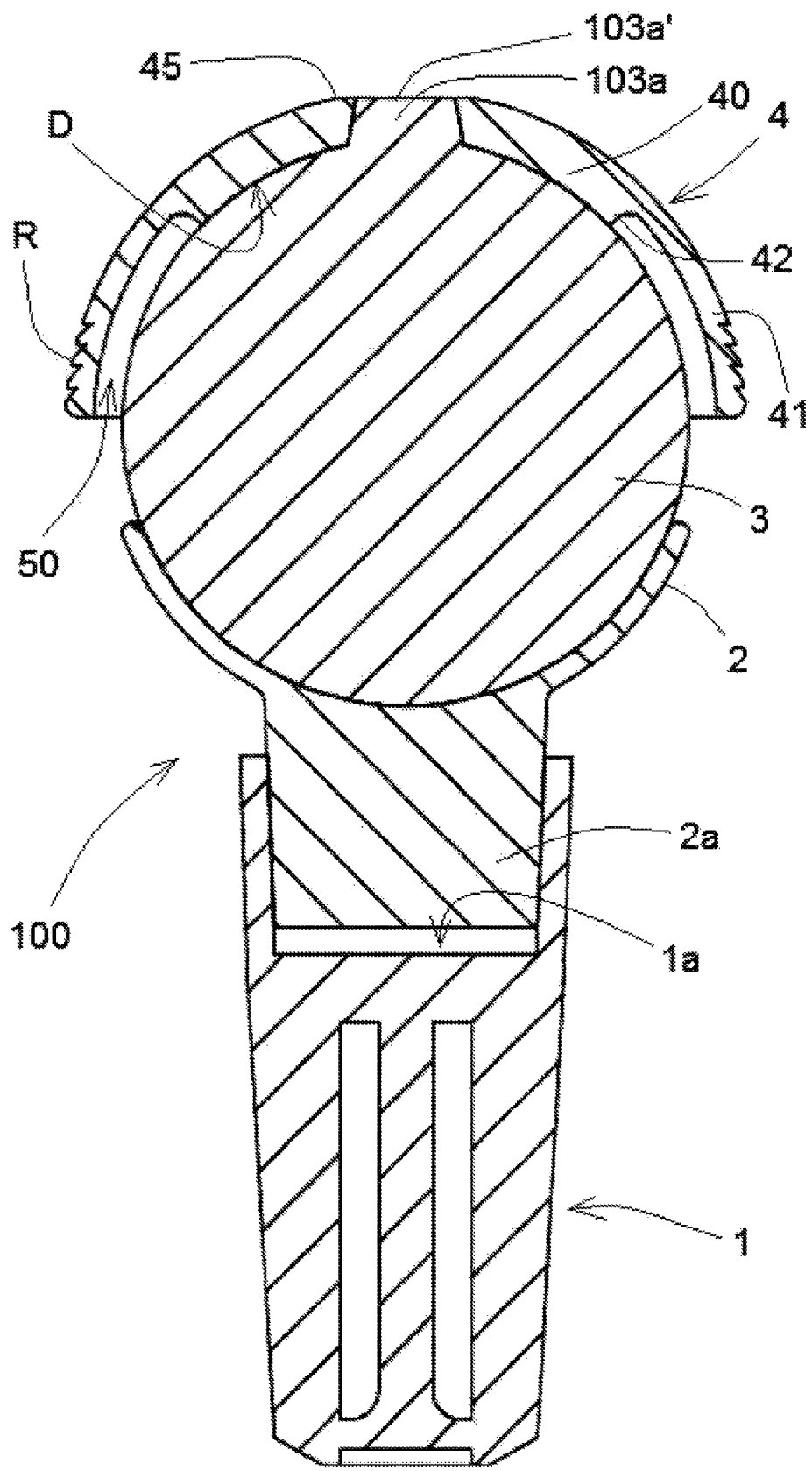
FIG. 9 is an axial sectional view of the prosthesis of FIG. 7 in assembled condition.

With reference to FIGS. 7 to 9 a version of the prosthesis (100) is disclosed. In such a version, instead of the hole (3a) shown in FIG. 3, the ball (3) comprises a truncated-conical shank (103a) that radially protrudes from the ball.

In this case, instead of the shank (4a) shown in FIG. 3, the prosthetic head (4) has a central hole (104a) obtained in the center of the flattened pole (45) of the prosthetic head. Therefore the shank (103a) of the ball is engaged in the central hole (104a) of the prosthetic head. The central hole (104a) of the prosthetic head has a truncated-conical shape in such manner to obtain a conical coupling with the shank (103a) of the ball.

Therefore the prosthetic head (4) is always tied to the ball (3). The spacing means (D) are formed by the central portion (40) of the prosthetic head that is stopped against the external surface of the ball (3) to generate the empty space (50) between the external surface of the ball (3) and the internal surface of the peripheral portion (41) of the prosthetic head. In fact, the distal cup (2) with slightly smaller dimensions than the empty space (50) must slide in the empty space (50). Moreover, the central portion (40) with higher thickness of the prosthetic head that is engaged on the ball (3) always acts as larger surface to discharge the forces between the prosthetic head and the ball and to allow for making balls with a large diameter.

The central hole (104a) of the prosthetic head is a through hole. The shank (103a) of the ball has a flat and planar end (103a') that is flush to the external surface of the flattened pole (45) of the prosthetic head.

Figure 10:
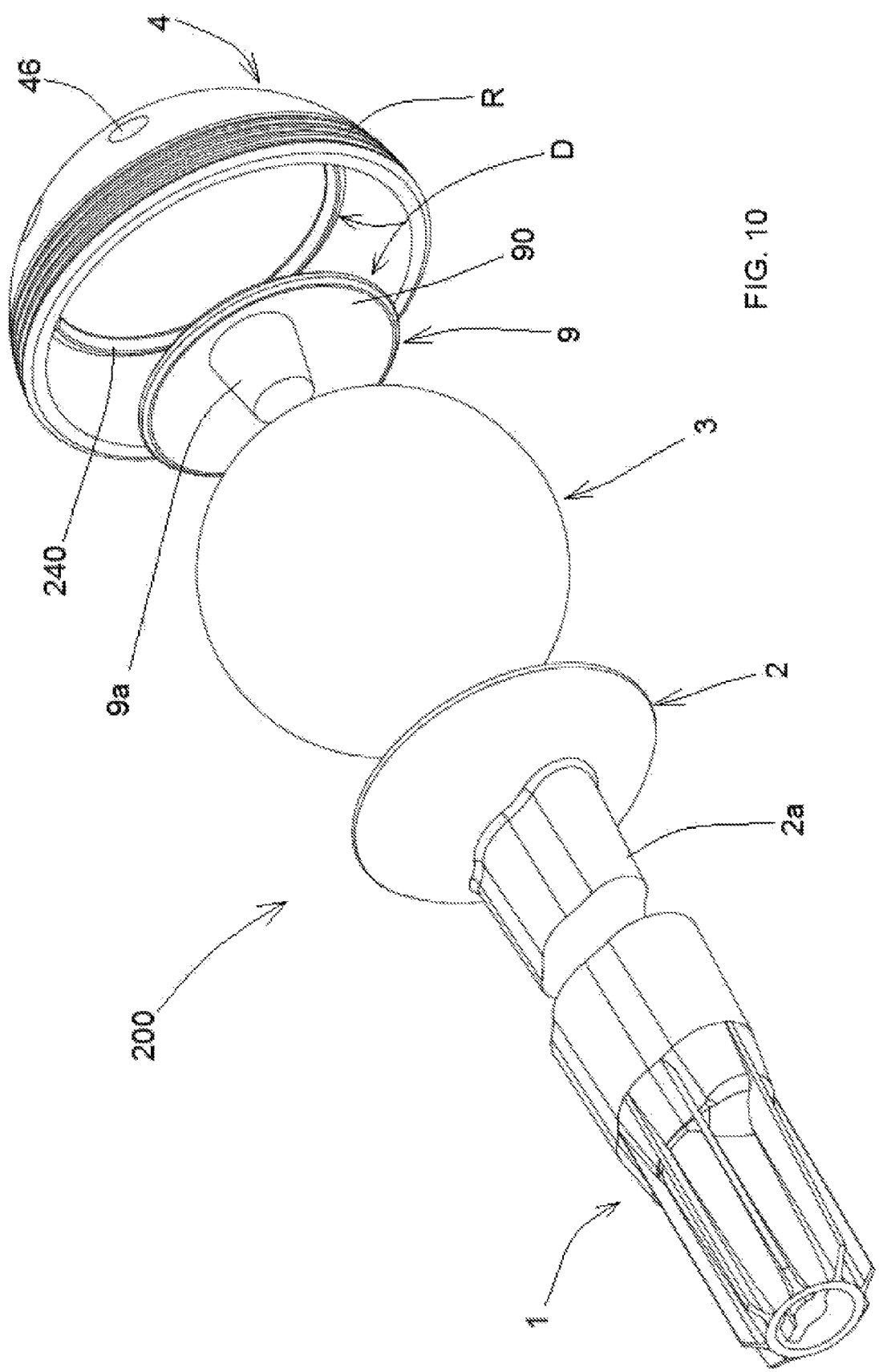
FIG. 10 is a perspective exploded view of a second embodiment of the prosthesis of the invention.
Figure 11:
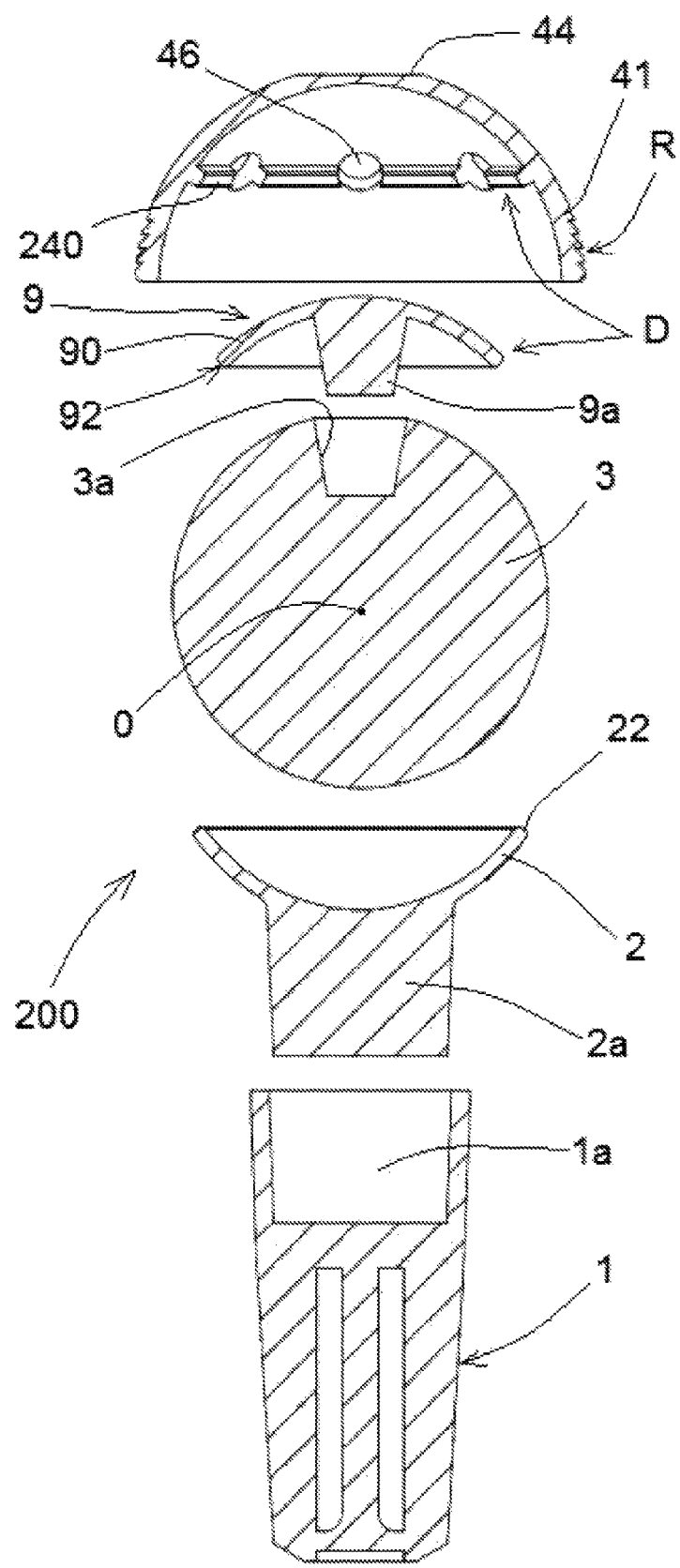
FIG. 11 is an axial sectional view of the prosthesis of FIG. 10.
Figure 12:
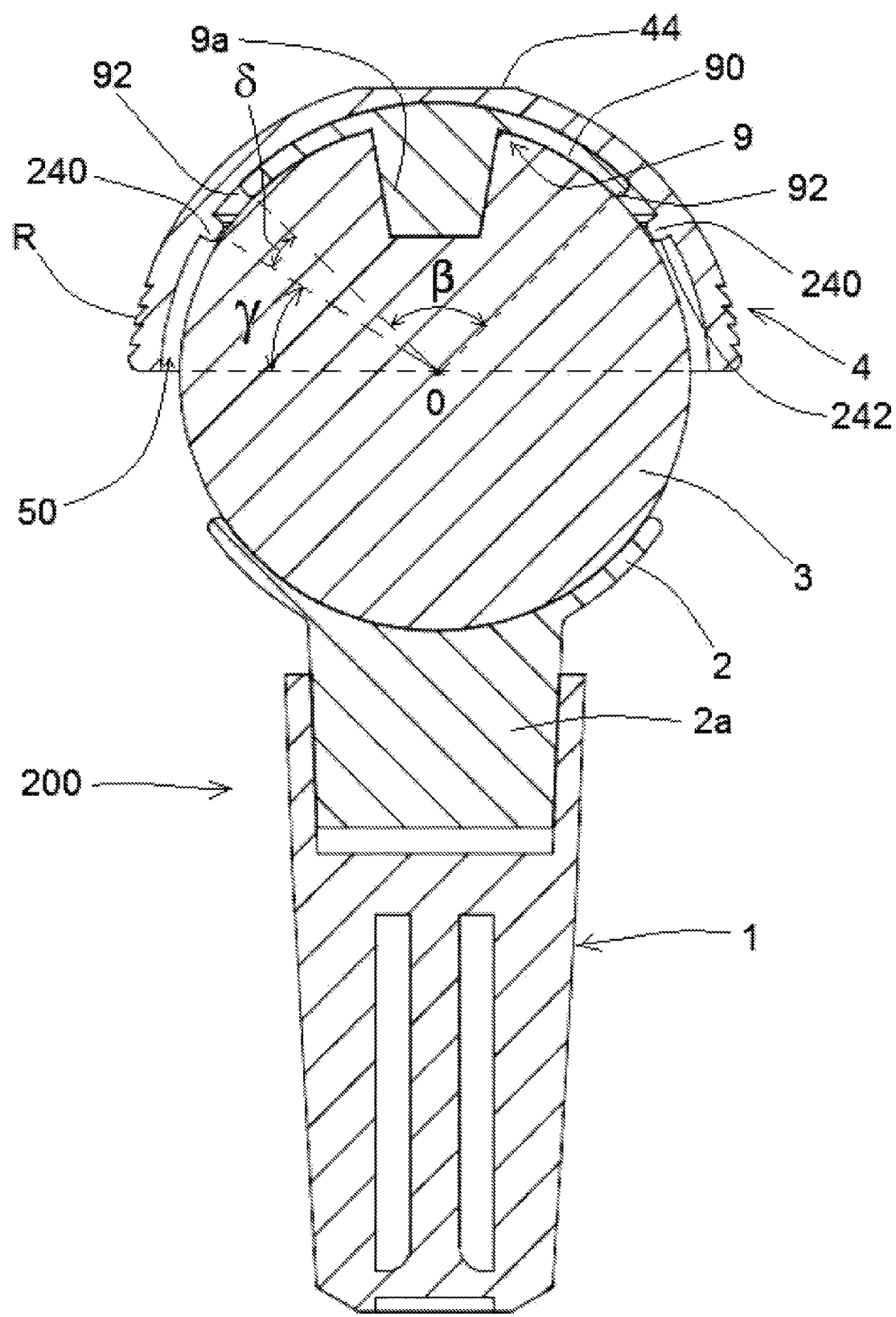
FIG. 12 is an axial sectional view of the prosthesis of FIG. 10 in assembled condition.

Referring to FIGS. 10 to 12, a second embodiment of the prosthesis, which is generally referred to with numeral (200). In the prosthesis (200), the prosthetic head (4) is not tied to the ball (3), i.e. the prosthetic head (4) and the ball (3) can move one with respect to the other. Such a solution provides a better distribution and a better discharge of the forces between the prosthetic head and the ball compared to the solution of FIGS. 1 to 9.

In such a case, the spacing means (D) comprise a modular spacing element (9) separated from the prosthetic head (4) and intended to be connected to the ball (3). The spacing element (9) comprises a spherical cap portion (90) provided with a concave surface towards the ball (3) and a convex surface towards the prosthetic head (4). The spherical cap portion (90) has a center that coincides with the center (O) of the ball. The concave surface of the spherical cap portion (90) has the same radius of curvature as the ball (3). The concave surface of the spherical cap portion (90) has a higher radius of curvature than the ball (3).

In this case the internal surface of the prosthetic head (4) has a hemispherical shape with the same radius of curvature as the convex surface of the spherical cap portion (90) of the spacing element. In this way, the prosthetic head (4) can slide on the spacing element (9).

The spacing element (9) comprises a shank (9a) that protrudes from the concave surface of the spherical cap portion (90) to engage in the hole (3a) of the ball.

The spacing means (D) also comprise a central portion (240) of the prosthetic head with higher thickness than the peripheral portion (41) of the prosthetic head, in such a way to define a step (242). The central portion (240) of the prosthetic head is engaged on the external surface of the ball (3) in such manner to generate the empty space (50) between the external surface of the ball and the internal surface of the peripheral portion (41) of the prosthetic head, in such manner that the border (22) of the distal cup is introduced in the empty space (50).

The holes (46) for the fixing screws are obtained in the central portion (240) of the prosthetic head.

The central portion (240) is a retaining collar that protrudes from the internal surface of the prosthetic head. Such a retaining collar embraces the spherical cap portion (90) of the spacing element in such manner to act as stop for the spherical cap portion (90) of the spacing element in order to prevent the prosthesis from dislocating when the prosthetic head slides with respect to the ball. In fact, the spherical cap portion (90) of the spacing element has a border (92) that is stopped against the retaining collar formed by the central portion (240).

As shown in FIG. 12, the spherical cap portion (90) of the spacing element is subtended by a central angle ($\beta$) comprised between 80° and 100°. In a vertical condition (when the axis of the shank (9a) of the spacing element coincides with the axis of the shank (2a) of the distal cup), the central portion (240) shaped as retaining collar is situated at an angular distance ($\delta$) of about 5-15° from the border (92) of the spherical cap portion (90) of the spacing element. Therefore the empty space (50) wherein the distal cup (2) slides is subtended by an angle ($\gamma$) comprised between 25 and 45°. In this way, the empty space (50) is sufficiently deep to receive the distal cup (2), avoiding all risks of dislocation and impingement.

Figure 13:
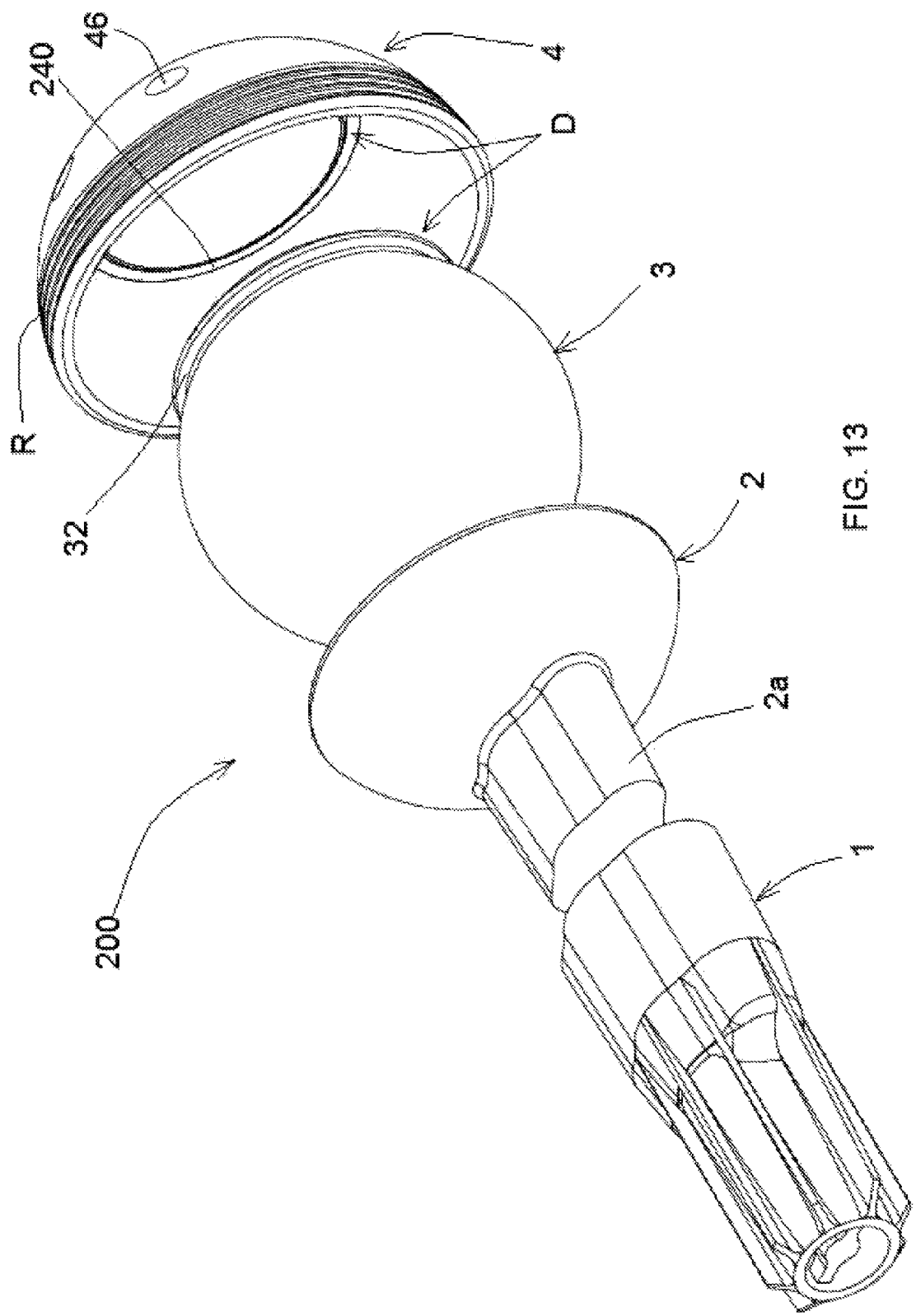
FIG. 13 is an exploded perspective view of a first version of the prosthesis of FIG. 10.
Figure 14:
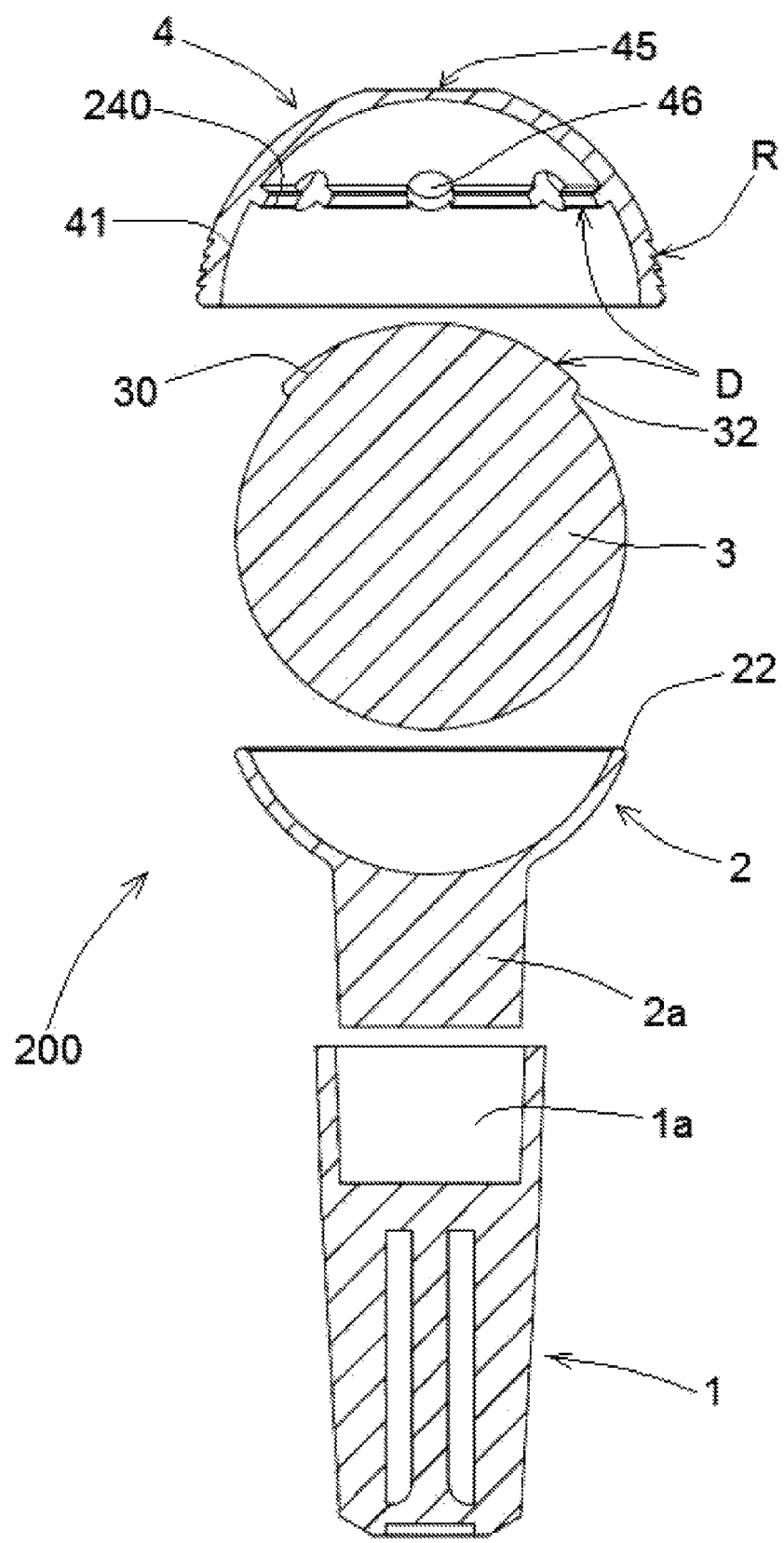
FIG. 14 is an axial sectional view of the prosthesis of FIG. 13.
Figure 15:
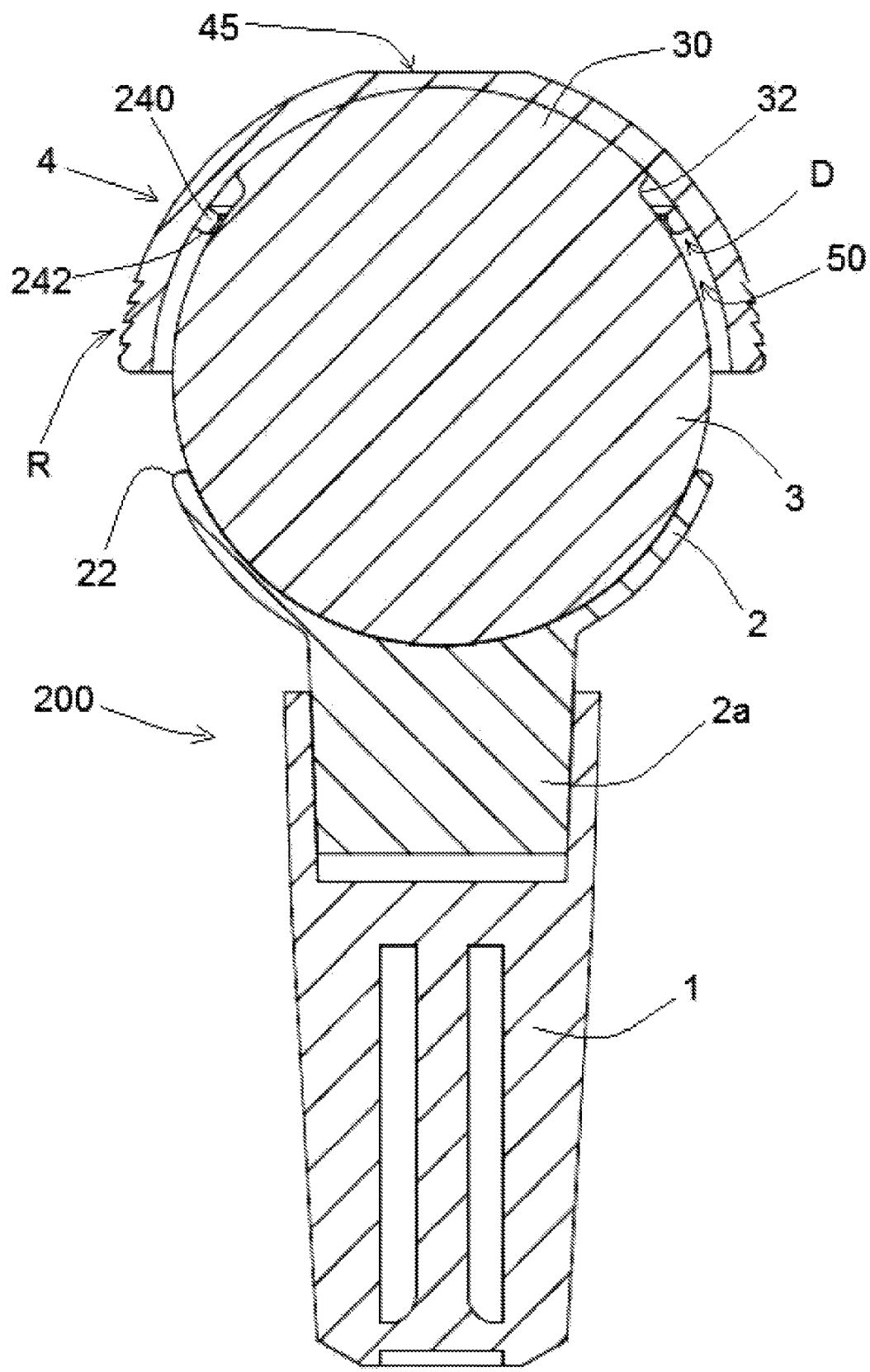
FIG. 15 is an axial sectional view of the prosthesis of FIG. 13 in assembled condition.

With reference to FIGS. 13 to 15 a first version of the second embodiment of the prosthesis (200) is disclosed. In this first version, the spacing means (D) comprise a spherical cap portion (30) obtained in one piece with the ball (3) in such manner to externally protrude from the ball (3), generating a stop border (32) contained inside the central portion (240) of the prosthetic head shaped as retaining collar.

Figure 16:
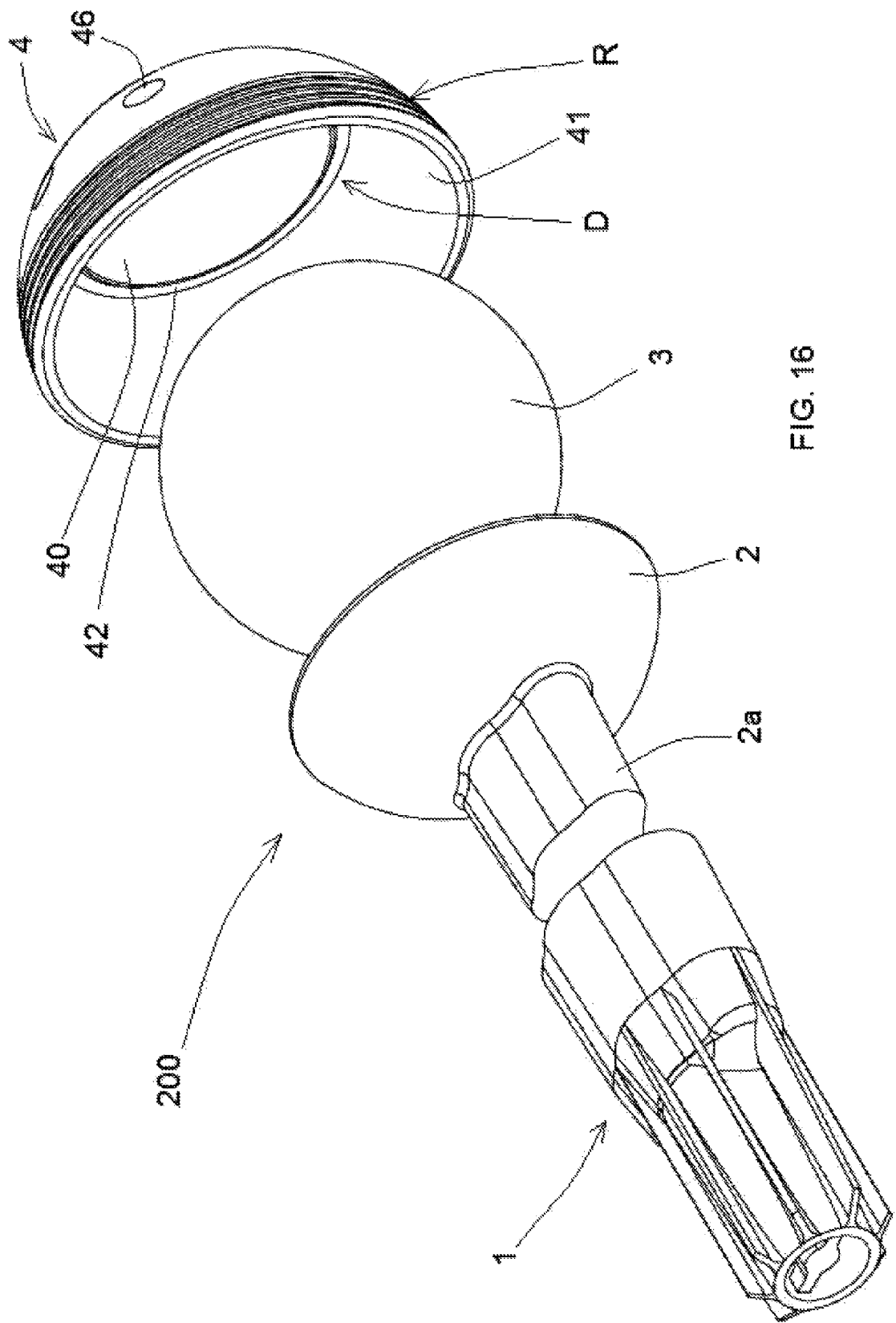
FIG. 16 is an exploded perspective view of a second version of the prosthesis of FIG. 10.
Figure 17:
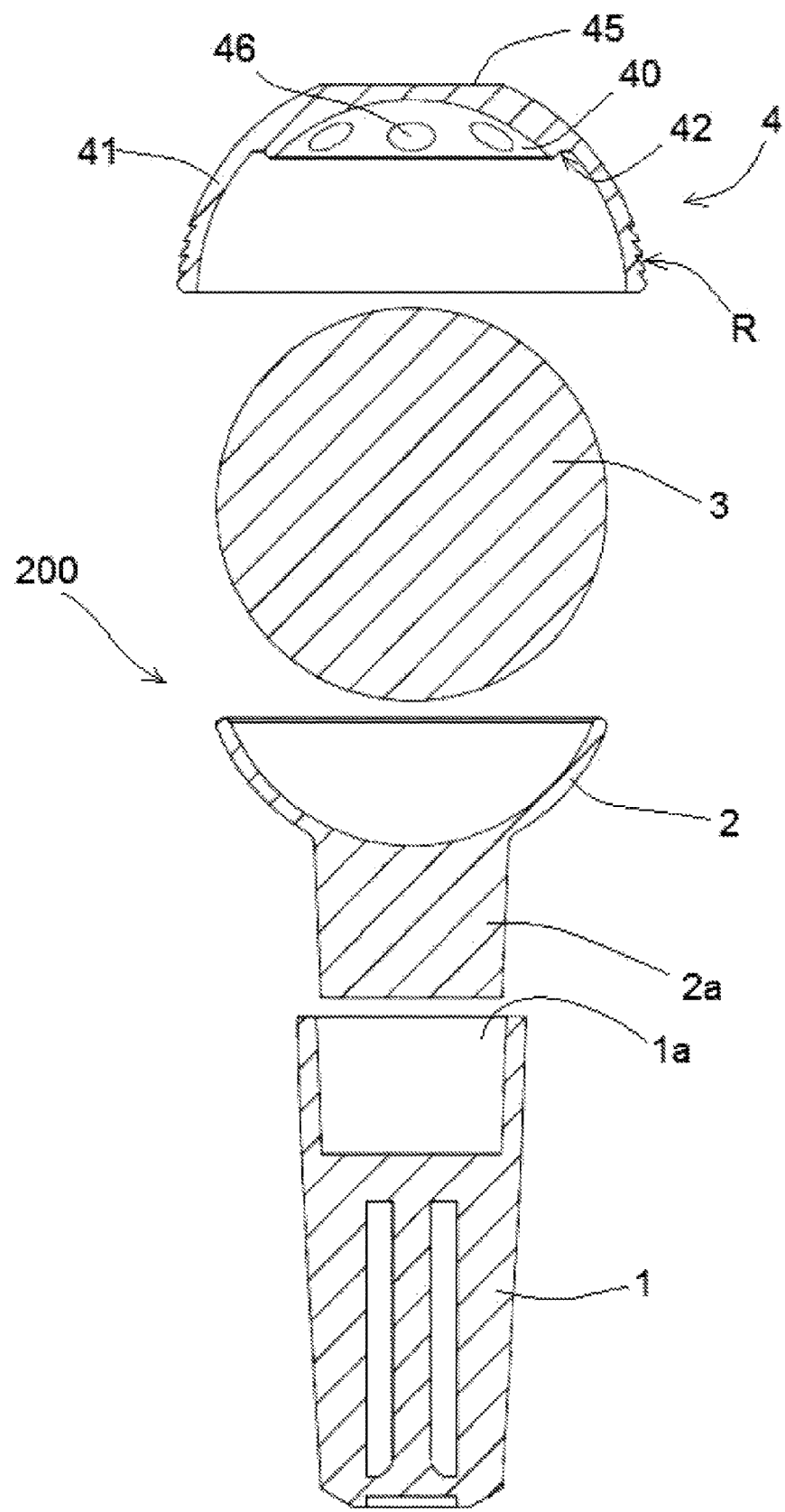
FIG. 17 is an axial sectional view of the prosthesis of FIG. 16.
Figure 18:
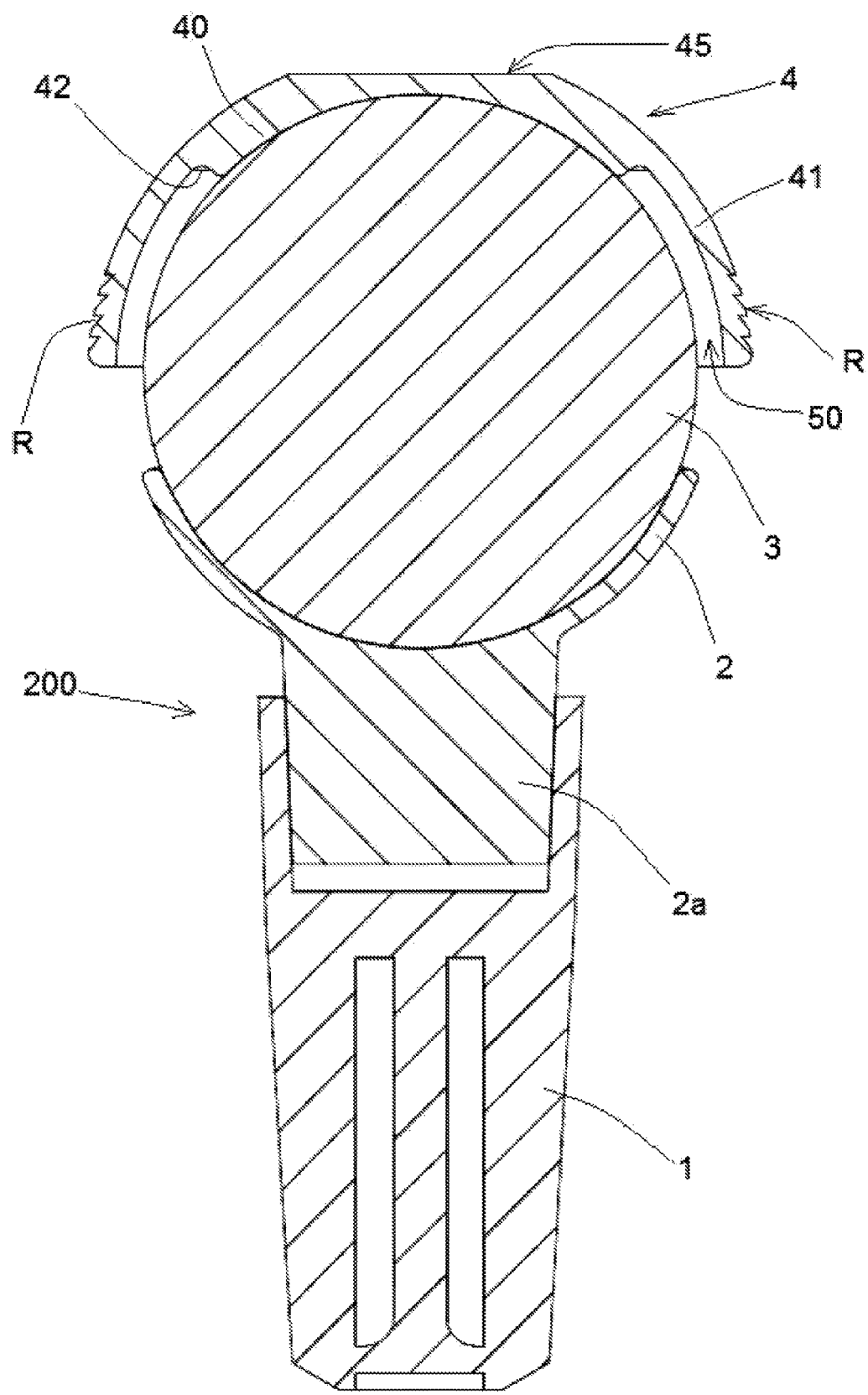
FIG. 18 is an axial sectional view of the prosthesis of FIG. 16 in assembled condition.

With reference to FIGS. 16 to 18 a second version of the second embodiment of the prosthesis (200) is disclosed. In this second version, the spacing means (D) comprise the central portion (40) of the prosthetic head, which in this case is a spherical cap portion obtained in one piece with the prosthetic head (4) (as in the embodiments of FIGS. 1-9), in such manner to protrude from the internal surface of the prosthetic head generating a step (42).

In all embodiments of the invention, the empty space (50) between the prosthetic head (4) and the ball (3) is created by a central portion (40; 240) of the prosthetic head (4) with higher thickness than a peripheral portion (41) of the prosthetic head.

When the central part (240) with higher thickness of the prosthetic head is a collar, a spherical cap element (90; 30) is disposed inside said collar and joined to the ball (3), with possibility of sliding with respect to the prosthetic head. In this case the collar-shaped central part (240) of the prosthetic head acts as stop to contain the movement of the spherical cap element (90; 30) joined to the ball (3).

The solutions of the present invention ensure a better distribution of the load applied on the prosthetic head (4) on the ball (3), without concentrating the load in a small area of the prosthetic head, as in the solutions of the prior art.

The solutions of the present invention allow for using balls with large dimensions, unlike the solutions of the prior art that use balls with small dimensions. Evidently, the use of balls with large dimensions (i.e. dimensions that are similar to the head of a femur) creates a more natural range motion for the patient.

I claim:

1. Hip prosthesis comprising:
   a stem intended to be inserted in a neck of a femur,
   a prosthetic head shaped as a substantially hemispherical cup, intended to be inserted in an acetabular seat, said prosthetic head comprising through holes to receive fixing screws intended to be fixed to said acetabular seat,
   a distal prosthetic component connected to the stem and shaped as a substantially hemispherical cup with concavity towards a concavity of said prosthetic head, said distal prosthetic component having a border,
   a ball disposed between said distal prosthetic component and said prosthetic head in such manner to generate a ball coupling,
   said prosthetic head comprising:
   a flattened pole defining an external central flat planar surface in order to adjust to various shapes of acetabular seat, and
   a central portion with a higher thickness than a peripheral portion of the prosthetic head, in such manner to generate a step inside the prosthetic head, said central portion of the head prosthetic head being engaged on the external surface of the ball in such manner to generate an empty space between the external surface of the ball and the internal surface of the peripheral portion of the prosthetic head, so that the border of said distal component is capable of introducing into said empty space, and
   grooves obtained on the external surface of said prosthetic head to allow for anchoring the prosthetic head to the acetabular seat in order to obtain a primary stability of the prosthetic head, wherein said through holes are exclusively obtained in said central portion of the prosthetic head and said grooves are exclusively obtained in said peripheral portion of the prosthetic head.

2. The hip prosthesis of claim 1, wherein said flattened pole of the prosthetic head is at a latitude of approximately 70-80°.

3. The hip prosthesis of claim 2, wherein said through holes of the prosthetic head are provided outside said flattened pole of the prosthetic head.

4. The hip prosthesis of claim 1, wherein said grooves of the prosthetic head are disposed starting from a lower edge of the prosthetic head and extend up to a latitude of approximately 20°-30°.

5. The hip prosthesis of claim 1, wherein said grooves of the prosthetic head comprise a plurality of circumferential ribs obtained as circumferential notches on the external lower part of the spherical cap and define a plurality of circumferential ribs.

6. The hip prosthesis of claim 5, wherein said circumferential ribs are tapered with increasing dimensions towards the lower edge of the prosthetic head and said circumferential ribs have a saw-tooth triangular section.

7. The hip prosthesis of claim 1, wherein said grooves of the prosthetic head define a helical thread that is wound around the external surface of the prosthetic head.

8. The hip prosthesis of claim 1, comprising a roughened surface obtained on the external surface of said prosthetic head.

9. The hip prosthesis of claim 1, wherein said prosthetic head is made of chrome-cobalt alloy or titanium alloy or Trabecular Titanium and has a coating of hydroxyapatite on trabecular titanium or porous titanium and hydroxyapatite.

10. The hip prosthesis of claim 1, wherein said prosthetic head is tied to said ball by means of a coupling between a shank obtained in the prosthetic head and a hole obtained in the ball or by means of a coupling between a shank obtained in the ball and a hole obtained in the prosthetic head.

11. The hip prosthesis of claims 1, wherein said prosthetic head is not tied to said ball and said central portion of the prosthetic head slides with respect to the surface of the ball.

12. The hip prosthesis of claim 11, wherein said central portion of the prosthetic head is shaped as a retaining collar that contains a spherical cap portion joined to the ball and externally protruding from the ball.

13. The hip prosthesis of claim 12, wherein said spherical cap portion is a separate element from the ball and is coupled to the ball.

14. The hip prosthesis of claim 12, wherein said spherical cap portion is made in one piece with the ball.

15. The hip prosthesis of claim 11, wherein said central portion of the prosthetic head is shaped as a spherical cap portion that internally protrudes from the prosthetic head in such manner to define said step inside the prosthetic head, wherein said central portion of the prosthetic head slides on the ball.

* * * * *